United States Patent [19]
Prywes

[11] Patent Number: 5,224,950
[45] Date of Patent: Jul. 6, 1993

[54] COLOR CALIBRATED MULTI-FUNCTION SCALPEL BLADE FOR INTRAOCULAR AND OTHER SURGERY AND ASSOCIATED METHODS OF USE

[76] Inventor: Arnold S. Prywes, 12 Jason Ct., Dix Hills, N.Y.

[21] Appl. No.: 770,185

[22] Filed: Oct. 2, 1991

[51] Int. Cl.⁵ .................... A61F 9/00; A61B 17/22
[52] U.S. Cl. .................... 606/166; 606/170; 606/172; 30/346; 30/289
[58] Field of Search ............ 606/166, 167, 170, 172, 606/161; 30/346, 351, 294, 289; 604/117

[56] References Cited

U.S. PATENT DOCUMENTS

| | | | |
|---|---|---|---|
| 1,527,561 | 2/1925 | Klum | 30/353 |
| 2,866,984 | 1/1959 | Plough | 30/289 X |
| 2,952,256 | 9/1960 | Meader et al. | 604/272 |
| 3,659,607 | 5/1972 | Banko | 606/170 X |
| 3,740,779 | 6/1973 | Rubricuis | 606/1 X |
| 4,324,044 | 4/1982 | Shahinian | 30/294 |
| 4,569,133 | 2/1986 | Schmidt | 606/172 |
| 4,688,570 | 8/1987 | Kramer et al. | 606/166 |
| 4,759,363 | 7/1988 | Jensen | 30/293 X |
| 5,071,427 | 12/1991 | Stahl | 606/172 |
| 5,135,530 | 8/1992 | Lehmer | 606/107 |
| 5,152,786 | 10/1992 | Hanna | 623/5 |
| 5,156,607 | 10/1992 | Kansas | 606/107 |

FOREIGN PATENT DOCUMENTS

| | | | |
|---|---|---|---|
| 2743336 | 3/1979 | Fed. Rep. of Germany | 606/167 |
| 439601 | 9/1948 | Italy | 30/289 |
| 3-128083 | 8/1991 | Japan . | |
| 8200759 | 3/1982 | World Int. Prop. O. | 606/166 |

Primary Examiner—Michael H. Thaler
Assistant Examiner—Mark O. Polutta
Attorney, Agent, or Firm—Ladas & Parry

[57] ABSTRACT

A scalpel for eye surgery having a blade member with a plurality of juxtaposed cutting sections arranged successively along the blade member. The cutting sections have respective cutting edges defining respective widths and lengths of incisions. Each cutting section is visually delineated from the other cutting sections by different coloration or other marking indicia, such that each cutting section will visually indicate the depth and width of an incision made by inserting the blade member into a body to the depth of the respective cutting section. The scalpel can include both a keratome type blade member and a scleral dissector blade member on a common support stem.

27 Claims, 7 Drawing Sheets

COLOR CALIBRATED MULTI-FUNCTION SCALPEL BLADE FOR INTRAOCULAR AND OTHER SURGERY AND ASSOCIATED METHODS OF USE

FIELD OF THE INVENTION

The invention relates to scalpel blades, specifically to an improved intraocular blade which is used for eye surgery, but also applicable for use in other surgical procedures.

The invention further relates to methods of use of the scalpel blades in eye surgery.

BACKGROUND

Cataract surgery is the most commonly performed operation in the United States. The term "cataract" refers to a condition in which the normally clear lens in the eye loses its clarity thereby producing visual loss. Recent advances in cataract surgery have allowed removal of the opacified lens through a small incision and replacement of the lens by a manufactured artificial lens or intraocular lens implant.

Typically, the ophthalmic surgeon makes one or two small (1.0-1.5 mm.) incisions initially into the eye to allow placement of small diameter surgical instruments or cannulas. These instruments allow the surgeon to perform an unroofing of the outer covering of the lens (lens capsule).

This procedure (capsulotomy) is effected under a protective gel (viscoelastic) which prevents the front of the eye or anterior chamber from collapsing.

After the conjunctiva is dissected with scissors, to dimensions allowing creation of a scleral incision of measured length and depth, hemostasis is obtained with a cautery or diathermy device. A scleral incision is then made after the conjunctiva has been recessed in order to allow access to the sclera. The sclera is dissected with a dissecting blade into the limbal are allowing entry of a small knife blade (1.0-1.5 mm diameter)

This initial incision must then be enlarged (3.0-3.2 mm.) to accommodate the placement of an instrument to remove the lens. The incision is once again enlarged (4.0-7.0 mm.) to allow insertion of the intraocular lens (IOL) within the original lens capsule. The viscoelastic is then removed and the sclera sutured to complete the procedure.

The procedure of cataract surgery is commonly performed with sterile, disposable scalpel blades to minimize the likelihood of infection.

Heretofore, scalpels of specific, standardized sizes and shapes were utilized in cataract surgery for each phase of the operation. The scalpel blades have been formed with many variations in shape, size and nomenclature. The type of blade commonly used for piercing the cornea and entering the anterior chamber is called a keratome. Keratomes of various profiles are known, each of which produces a measured, standardized incisional width. The cataract surgical procedure requires keratomes of different sizes to produce a measured incision. Alternatively, rulers or calipers which measure the length of an incision, may be used along with scissors or non-calibrated scalpels in order to enlarge an incision. The use of multiple, differently configured scalpel blades for different phases of the surgical procedure is costly. It requires that the surgeon change instruments when proceeding from one phase of the incision-making procedure to the next.

In one conventional embodiment of a piercing blade, a "needle-knife" (after Ziegler) is used to penetrate the cornea. Other lancet blades exist under the names of various manufacturers. One such embodiment is a "V-Lance" manufactured by Alcon Ophthalmic which comprises a honed tip which is tapered and affixed by a metal shaft to a plastic handle. The dimensions of the blade allow entry into the cornea for producing a small (1.5 mm) incision which is beveled and self sealing. These blades are not useful for enlarging incisions because they are not sufficiently sturdy. They also require measuring devices to determine the width of the incision.

In another embodiment known as a "#57 Beaver Blade", a tapered, honed "hockey stick" shaped blade is used to dissect scleral tissues with sterile, disposable blades and reusable, sterilizable handles. This blade is not useful for initiating a corneal incision or for enlarging it since it requires the use of a ruler or caliper. It is too blunt to make a precise piercing incision.

In another embodiment, a "Guardian Scalpel" manufactured by Myocure, allows scleral incisions employing a plastic sleeve whereby penetration to a precise depth is assured. However, it is not sufficiently precise for enlarging an incision beyond its initial width without a caliper or ruler. It is not useful for dissection of a scleral pocket.

In another embodiment, a blade manufactured from a sliver of diamond attached to an autoclavable holder with or without a micrometer attachment is used to produce incisions of proper depth. These "diamond knives" are of fixed width but adjustable depth. These blades are not disposable and are quite expensive. They are subject to breakage if not handled with great care. A caliper or measuring device is similarly required to enlarge an incision.

In another embodiment, a "Phako-Keratome" produces incisions into the anterior chamber after a scleral flap of tissue or scleral pocket is dissected. This blade produces an incision of specific width and is disposable, sterile and can be placed on a single use or reusable handle. The fixed width of this blade is accurate only for the initial incision. A ruler or caliper must be used to measure the length of incisions being enlarged with this instrument. It is not useful for dissecting scleral flaps.

The evolution of small incision surgery was developed with refinements in the procedure over many years. A few years ago cost containment in these procedures was not a major factor since the cost of such procedures and of disposable blades were reimbursed by third party payers. In the present era of escalating costs for health care, with decreasing reimbursements, the need for reducing the cost of disposable items, i.e. blades and instruments has become a factor in seeking the design of a multi-purpose blade. In the current state of the art, the blades are of single use and disposable and different blades are required for each phase of the cataract procedure.

Recent advances in cataract surgery have made it possible to implant intraocular lenses through small incisions. This requires that a scleral flap or pocket be dissected in order to allow the incision to be self sealing, or require a minimum number of sutures.

A scleral groove is formed in the sclera, at a measured distance from, and parallel to, the corneal limbus. The depth of the scleral incision is usually estimated by the surgeon The sclera is only 0.6 mm. in thickness at the limbus of the eye and may vary in thickness in some patients with ocular disease. If a surgeon wishes to make a 200 micron or 400 micron deep scleral groove prior to fashioning a scleral flap or pocket, a simple method of gaging the depth of this groove is desirable. Some scalpel blades have guards on them in order to prevent making this groove too deep (Myocure). Some use a micrometer attached to a guarded scalpel to allow continual adjustment of the incisional depth (diamond knives).

A simple, visually apparent method of performing this task (while not requiring that the scalpel be removed from the incision) to measure the depth of the groove would be advantageous.

Presently, blades with guards are the only way to judge the depth of an incision accurately. A blade which provides this feature without the use of a guard would be very desirable.

The groove is then dissected toward the limbus until the anterior aspect of the limbus is reached maintaining a constant scleral thickness and forming a "pocket". These scleral pocket-type incisions require a blade of tapering edge thickness in order to allow gradual and controlled incisions. The desired distance from the limbus of this initial groove may vary from one surgeon to another. Some surgeons place incisions anteriorly at the imbus, some posteriorly. The distance from the limbus in a posterior scleral pocket incision may range from 1.0-4.0 mm. A caliper, ruler or other measuring device is required to determine and verify its location.

A scalpel blade which could make this incision and act as its own "visual" caliper would obviate the need for an assistant to measure the distance from the limbus (sometimes repeated measurements are required). The surgeon's ability to monitor the length of the incision while placing the incision would help to expedite the performance of the procedure.

Once the scleral groove is complete, the "pocket" is fashioned by the dissecting blade. A planar dissection is made by using the dissecting blade to "tunnel" a pocket of measured depth into the sclera.

Presently, guarded scalpels require that the guard be removed in order to perform this "tunnelling" maneuver. A blade which uses no guard but provides the capability of forming a pocket of measured depth would be greatly beneficial.

An entry into the anterior chamber through the cornea is made to allow bimanual manipulation of the cataractous lens. A separate 1.0-1.5 mm. wide blade of tapered dimensions and of approximately 1.0 mm length is usually used. The scleral pocket is then entered with a keratome of 3.0-3.2 mm. This allows the use of a cannula which infuses a viscoelastic gel. The gel is instilled in order to allow the central anterior lens surface to be removed in a controlled manner (capsulotomy), without loss of anterior chamber depth.

A lens removal device such as a phakoemulsifier, etc. is then introduced through this measured incision. After the lens is removed, a scissors or a keratome is used to enlarge the incision. If a scissors is used, this requires that a caliper or ruler be employed. If a keratome is used initially, a second keratome of larger size is used at this time to enlarge the incision to accommodate the diameter of a lens implant of the required size.

Each of the incisions and the procedure of lengthening the scleral pocket has heretofore required the use of several different disposable scalpel blades of specific size. This increases the cost of performing the procedure, as well as requiring the changing of blades.

SUMMARY OF THE INVENTION

An object of the invention is to provide a single scalpel for producing correctly sized incisions for the individual phases of the cataract surgical procedure.

A further object of the invention is to provide a scalpel for producing precise surgical incisions outside of and within the eye.

Another object of the invention is to provide a scalpel capable of effecting multiple operations in producing incisions of different dimensions and eliminating the need for additional measuring devices and additional blades.

A further object of the invention is to provide a scalpel having a blade which is capable of forming an incision to a depth which is indicated by the blade itself, while remaining in the incision, thereby obviating the need for separate means for measuring the incisional depth or for removal of the blade from the incision to carry out the measurement, this being achieved without the need to use guards or other means to limit the depth of penetration of the blade.

Another object of the invention is to provide a dissecting blade for effecting a tunneling operation in the sclera to form a pocket whose depth can be determined visually in the course of the tunneling operation without the use of guards or separate measuring instruments.

In order to satisfy the above and further objects, the invention contemplates a scalpel comprising a blade member including a plurality of juxtaposed cutting sections arranged successively along the blade member, said cutting sections having respective cutting edges defining for said cutting sections respective widths and lengths and means associated with each of said cutting sections for visually delineating said sections from one another such that each cutting section will visually indicate the depth and width of an incision made by inserting said blade member into a body to the depth of the respective said cutting section.

In accordance with the invention, the means for visually delineating the sections from one another may comprise a different surface marking such as a different color for each section and/or a different shape for each section.

In further accordance with the invention, the blade member may have a pointed tip for piercing operations, such as corneal and scleral incisions, or it may have a rounded tip for forming a scleral groove and for dissecting the sclera to form a scleral pocket.

In the embodiment with a pointed tip, the cutting sections increase in width as they are more distant from the tip so that when the blade member is inserted to the depth of a particular cutting section, the depth and width of the formed incision will be indicated by the color of the particular cutting section. Namely, the cutting sections are calibrated as regards width and depth so that when a particular cutting section is at the entry site of the formed incision, it will provide a measure of the depth and width of the formed incision.

In the embodiment with the rounded tip, the width of the blade member is substantially constant allowing formation of a scleral pocket of uniform width, the depth of said pocket i.e. the distance of insertion of the blade member, being visually indicated by the particular cutting section disposed at the entry site of the incision.

In further accordance with the invention, the scalpel comprises two blade members on a common stem or shaft, one blade member having a pointed tip and tapered aspect for corneal and scleral incisions whereas the other blade member has a rounded tip and straight aspect for scleral dissection.

DETAILED DESCRIPTION

Figure 5:
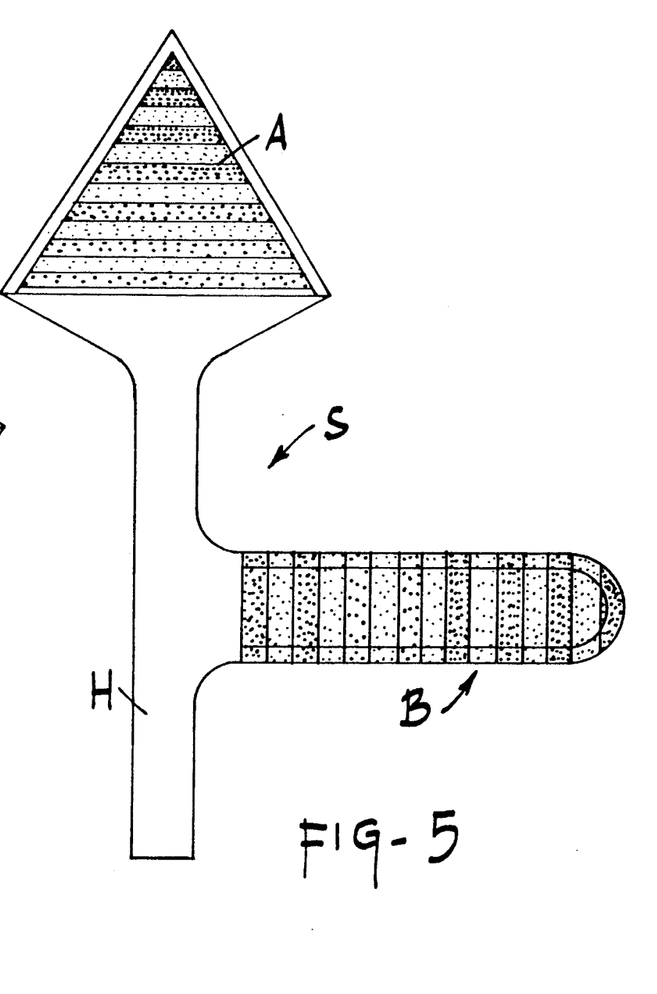
FIG. 5 is an enlarged elevation view of a scalpel which includes the blade members of FIGS. 1 and 3.

FIG. 5 shows a scalpel S for eye surgery having a stem or shaft H from which two blade members A and B extend approximately perpendicularly to one another. The blade member A has a pointed tip and tapered aspect suitable for piercing tissue and forming incisions in cataract and intraocular surgery whereas blade member B has a rounded tip and straight aspect suitable for scleral dissections. The operations with the blade members A and B will be explained in more detail later.

Figures 1, 7:
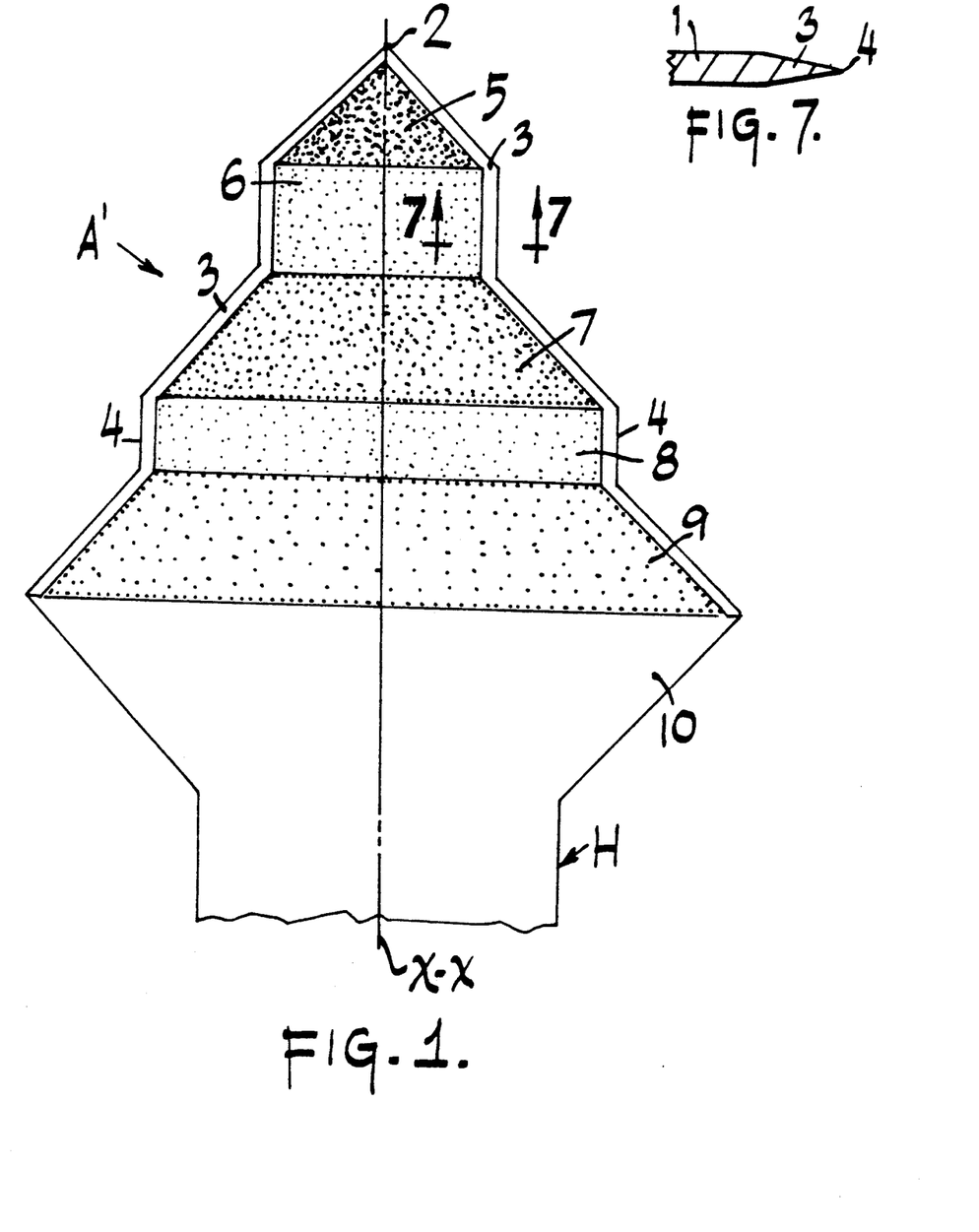
FIG. 1 is an enlarged elevation view of a detail of a blade member of a scalpel for eye surgery.
FIG. 7 is a sectional view on further enlarged scale taken along line 7—7 in FIG. 1.

FIG. 1 shows a blade member A' which is a modification of the blade member A in FIG. 5. The blade member A' is constituted as a thin, flat, rigid blade 1 made from a material, such as stainless steel, having a thickness in the range of 0.001 to 1.0 mm. and particularly of about 0.1 mm. The thickness of the blade is sufficient to resist bending. The blade may be made of other material such as gemstones, ceramics, other metals such as aluminum, titanium, etc. composites, plasticized or laminated materials, colloids such as glass etc. or any other materials which may be sharpened, etched, or colored and maintain rigidity and tensile strength.

The blade member A' has a pointed tip 2 and is generally symmetrical about axis X—X extending longitudinally of the blade and passing through pointed tip 2. The blade 1 has a perimetral edge portion 3 which is precisely honed to form a taper defining a cutting edge 4 around the perimeter of the blade. The perimetral edge portion 3 is about 0.05 mm wide.

The blade member A' comprises a succession of juxtaposed sections 5, 6, 7, 8, 9 serving as cutting sections. Section 5 is a triangular section with tip 2 at its apex and cutting edge portions 3 at its sides. Section 6 is rectangular with parallel cutting edge portions 3 at its lateral edges. Section 7 is trapezoidal with angulated cutting edge portions 3 at its lateral sides which taper so that cutting section 7 widens in the direction from the tip end of the blade member towards its opposite end where the blade member joins the stem H. Section 8 is a rectangular cutting section similar to section 6 and section 9 is a trapezoidal section similar to section 7. Section 9 is joined to stem H by a section 10 of reverse trapezoidal shape that narrows in width in the direction from tip 2 to stem H. The section 10 is not honed at its lateral edges and therefore does not constitute a cutting section.

In the preferred embodiment, the sections 5-10 are respectively and individually delineated by suitable marking means so that each section is readily distinguishable from the others. The marking means for delineating the sections from one another can be achieved in various ways, such as by surface etching or markings, but preferably the surfaces of the sections are formed of different colors so that they can be readily distinguished. All sections have precise dimensions of axial length and width.

The blade member A' can be used to form incisions, such as in the cornea or sclera, of different width and depth. Thus, when cutting section 5 is inserted into the eye to its full depth, an incision will be made having a width equal to the width of the base of section 5 and a depth equal to the height of section 5. For greater incisional depth, the blade member A' can be inserted, for example, to the full depth of section 6. The incision will not be widened and such an incision can be used for introduction of intraocular fluids or instruments into the eye. If the blade member is inserted to still greater depth, for example, through the full depth of section 7, the incision is further widened for introduction of larger instruments, for example, to remove cataracts i.e. phakoemulsifier etc. Section 6 will be visible when viewed through the transparent cornea during corneal incisions to indicate its penetration therein. Upon reaching the end of cutting section 5, the marking or color of cutting section 6 can be easily detected by being seen internally through the cornea or detected externally when cutting section 5 is no longer visible from outside the eye while section 6 remains in view.

The honed edge portion 3 of cutting section 6 allows smooth penetration of the piercing tip 2 to produce an incision of a width of fixed size. In this embodiment, an incisional width of 1.5 mm. and a depth of 1 mm. is obtained when cutting section 6 is fully inserted The end of section 6 also denotes the beginning of section 7, which is distinguished by a different color or marking. The lateral edge portions of section 7 are honed to form cutting edges which are angulated to produce an incisional width of fixed but large dimension, in this embodiment, 3.0 mm. to allow the introduction of the phakoemulsification tip to remove cataracts.

The end of cutting section 7 is separated from the widening edge portions of cutting section 9 by rectangular section 8 which prevents an abrupt enlargement of incisional width. This is accomplished by the rectangular configuration of section 8 and the vertical orientation of its honed edges 4 which can be viewed internally through the cornea once the incision has been enlarged. In this embodiment the incisional width will remain enlarged to 3.0 mm from 1.5 mm.

The beginning of section 9 with its angulated honed edges 4 is delineated by a transition to a different color or marking, which is viewed until the desired incisional width is accomplished and section 10 is viewed at the entry site of the incision after the insertion of section 9. The honed edge 4 of section 9 cuts an incisional width of 5.0 mm. in this embodiment, but could be configured to varying specific widths.

The edges of section 10 are angulated at ninety degrees relative to the honed edges 4 of section 9. This demarcation of section 9 from section 10 is visible internally and externally of the eye by the transition in color or marking of sections 9 and 10. When the transition is seen at the entry site of the incision, the blade member is withdrawn, having made the proper incisional width. The blade stem or shaft H can be attached to a handle (not shown) which may be disposable or reusable. The blade stem may be permanently attached to the handle and be entirely disposable, or the blade may be separate and attachable to a reusable handle. The handle or the shaft may be uniplanar or angulated.

The dimensions of the blade may vary from one configuration to another. In the embodiment shown in FIG. 1, the width of the blade at the base of section 9 is 5 mm, and excluding the honed edge portion 3 is 4.9 mm. The width of section 8 is 3 mm. and without the honed edge portion is 2.9 mm. the width of the base of section 5 is 1.5 mm and without the honed edge portion is 1.4 mm. The width of the blade stem H is 2.5 mm.

Figure 2:
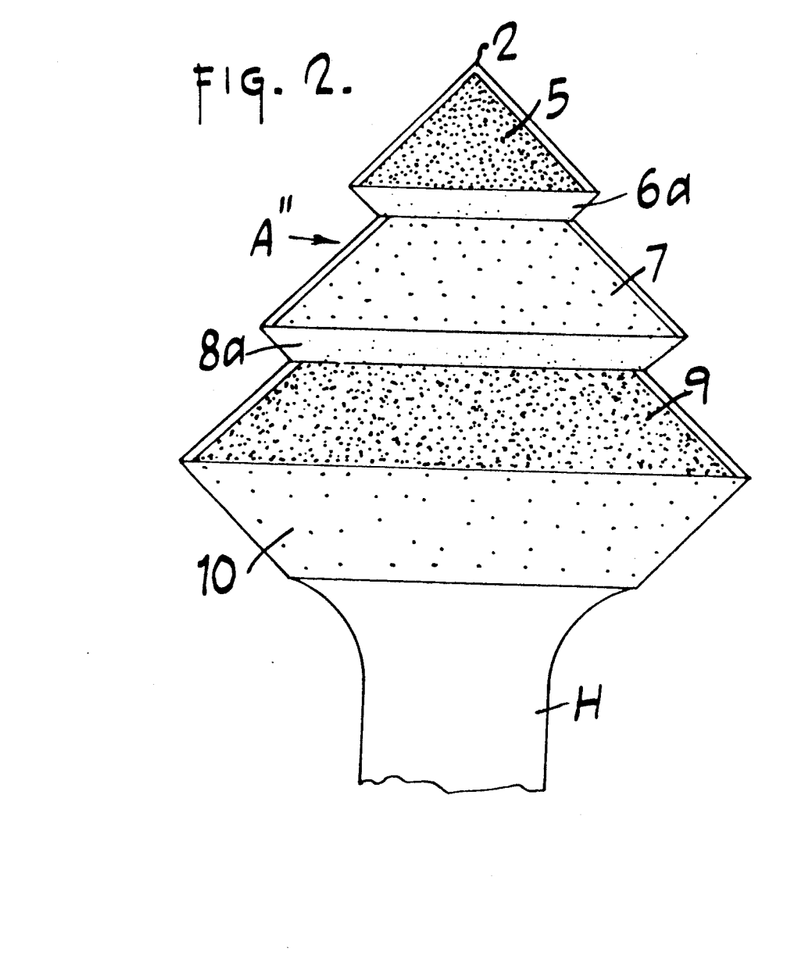
FIG. 2 is similar to FIG. 1 and shows a modified embodiment of the blade member.

A blade member A" in FIG. 2 is similar to that in FIG. 1 and the same elements are given the same reference numerals. Thus, blade member A" has successive cutting sections 5, 7, 9. However, instead of joining these cutting sections with rectangular cutting sections 6 and 8 as in FIG. 1, cutting sections 5, 7, 9 are respectively connected by sections 6a and 8a which are not honed at their edges. Sections 6a and 8a have lateral edges which taper inwardly to form reverse trapezoidal shapes for sections 6a and 8a. Hence, as the blade member is pushed more deeply into the incision, the incision is widened by the cutting edges at the sides of sections 5, 7 and 9 whereas when the sections 6a and 8a enter the incision no further cutting is effected and the reverse taper of sections 6a and 8a insures that no resistance to continued insertion of the blade member into the incision will take place until the cutting edges of the next cutting section come into contact with the tissue at the incision. The depth of entry of the blade member and the width of the incision will be determined visually by viewing the extent of the blade member within the eye when able, for example, through the transparent cornea or by viewing the section of the blade member disposed at the entry site of the incision.

Figure 3:
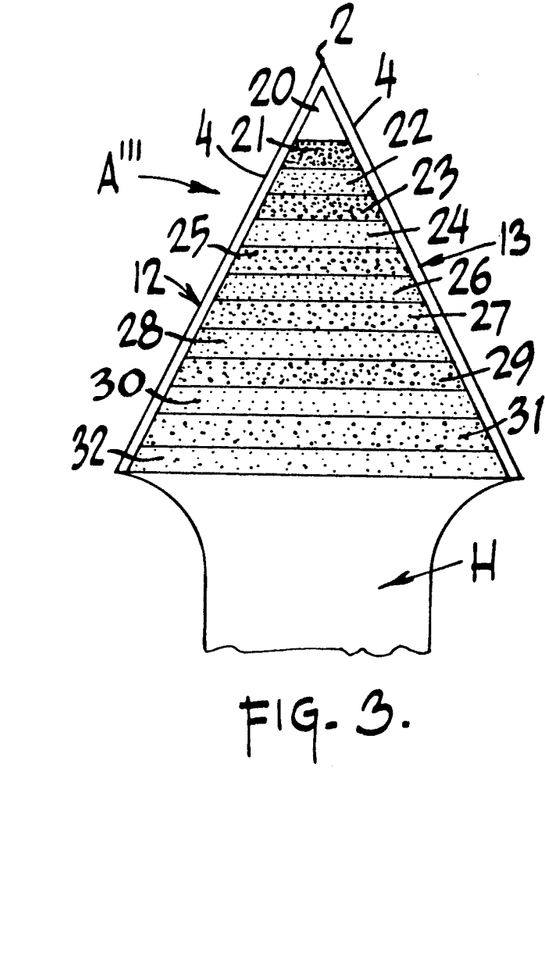
FIG. 3 is similar to FIG. 1 and shows another modified embodiment of the blade member.

FIG. 3 shows a blade member A‴ according to another embodiment in which the blade member is of triangular outline. As in FIGS. 1 and 2, the blade member has a pointed tip 2 for piercing and cutting. The sides 12, 13 of the blade member A‴ are formed as tapered edge portions with cutting edges 4. The blade member A‴ is divided into thirteen cutting sections 20–32. Section 20 is triangular and sections 21–32 are in the form of trapezoidal strips. The base of triangular section 20 is 1.5 mm in length and the height of triangular section 20 is 1.0 mm. Therefore, when triangular section 20 has been fully inserted, an incision is formed of the cutting sections 21–32 is 0.5 mm wider than the top of the respective cutting sections and each cutting section has a height of 0.33 mm. Therefore, as each strip is inserted, the incision is widened by 0.5 mm and deepened by 0.33 mm. Suitable indicia can be placed on the blade member to indicate the periodic variation in width and depth at the base of each cutting section and/or the total width and depth measured from tip 2. However, the width and depth of the incision can be determined without such indicia. In a particular embodiment, widths of common usage such as 1.5 mm, 3 mm, 6 mm, etc. can be highlighted, for example, by prominent coloration to make this distinctive relative to the other strips. Hence, by observation, the surgeon will readily have, as benchmarks, these specific widths. In the embodiment given, if distinctive prominent marking is provided for the sections denoting 1.5, 3 and 6 mm widths, there will be two strips of 0.5 increment in width between the 1.5 mm and 3 mm widths and five strips between the sections of 3 mm and 6 mm widths. The estimation of the exact width of an incision can therefore be made rapidly by viewing a benchmark width and the number of strips therefrom to the incision. In actual use, the evaluation of the incisional width is done without conscious thinking and is substantially immediate. No calculation or estimation or reference to extrinsic measuring devices such as calipers or rulers is necessary. The determination of the incisional width takes place in the brain in a manner similar to the mental processes of telling time from the position of clock hands without resort to numerals or other indicia.

Figure 3A:
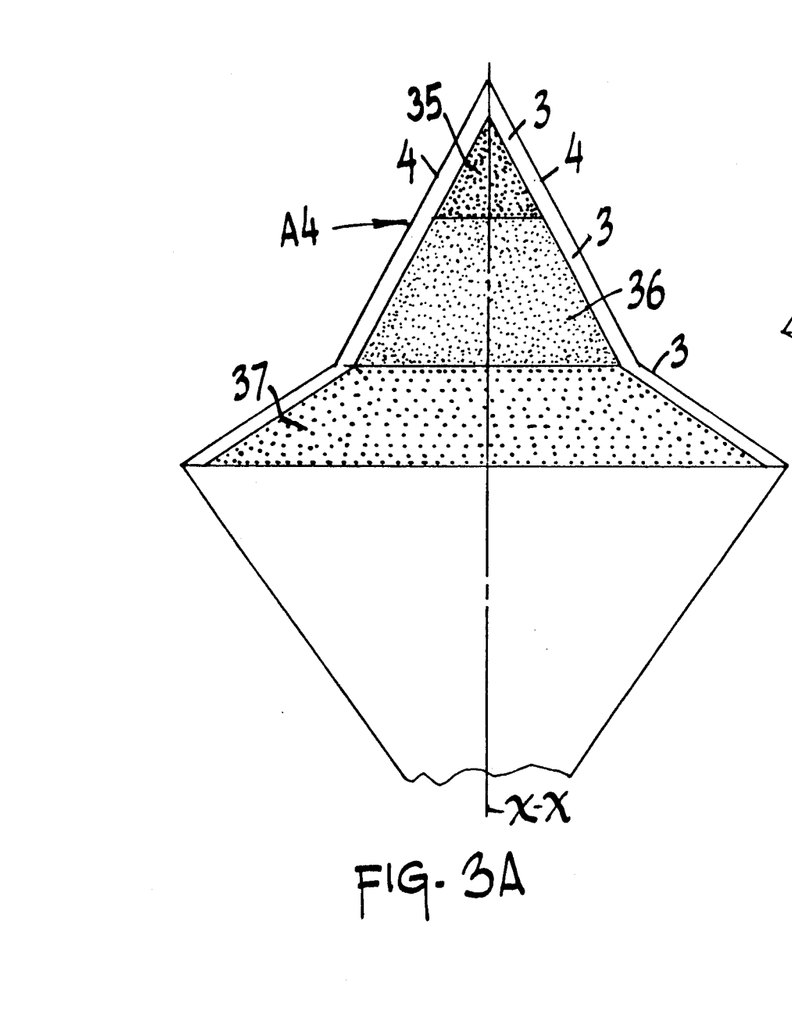
FIG. 3A is similar to FIG. 3 and shows a modification of the blade member therein.

FIG. 3A shows a blade A4 similar to the blade in FIG. 3 having three distinct cutting sections 35, 36, and 37. The cutting edges 4 have a straight, continuous taper along sections 35 and 36 and at the transition between sections 36 and 37, the cutting edges 4 increase in taper to produce a greater increase in cutting width for section 37. By way of example, the blade A4 can produce incisions of a width of 1.5 mm at the base of section 35, a width of 3.0 mm at the base of section 36, and a width of 6.0 mm at the base of section 37. Sections 35 and 36 each have a height (measured along the axis X—X) of 1.5 mm and section 37 has a height of 1.0 mm.

In the embodiments of FIG. 1, 2, and 3 the blade member is provided with cutting sections having visual distinction based on distinguishable marking means as well as shape differences. Hence, in FIGS. 1 and 2 cutting sections 5, 7 and 9 are readily discernable by virtue of being set apart in a distinctive way which will be readily apparent to the surgeon without need for extrinsic measuring means. The intermediate sections 6 and 8 in FIG. 1 and 6a and 8a in FIG. 2 constitute buffer sections which do not widen the incision when the blade member is pushed more deeply into the incision They also serve as a separation means to set the cutting sections apart in a visually distinctive fashion.

Figure 4:
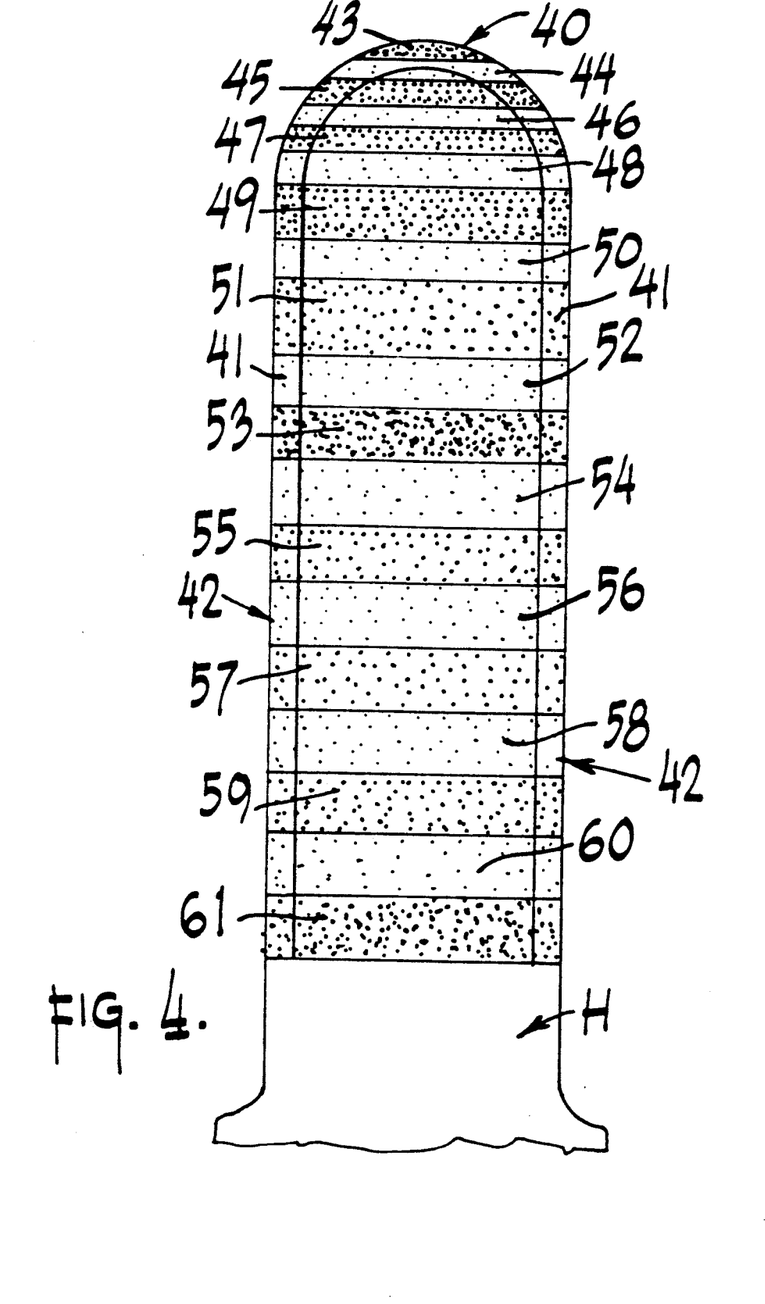
FIG. 4 is an enlarged elevation view of a detail of a further embodiment of a blade member.

FIG. 4 shows blade member B constituted as a thin flat rigid blade similar to the blade members of FIGS. 1-3. Instead of having a pointed tip as in these blade members, blade member 8 has a rounded end 40 of substantially circular outline. The blade member B is intended as a scleral dissector for forming a pocket in the sclera. At the perimetral edge of the blade member B, a tapered edge portion 41 is formed which extends uniformly around the perimeter of the blade member B and defines a sharp cutting edge 42. The edge portion 41 of blade member B is similar to the edge portion 3 of the blade members in FIGS. 1-3. The blade member B is divided into nineteen transverse cutting sections 43–61. Section 43 has the shape of a segment of a circle, sections 44–48 are in the form of strips having lateral edges of part-circular shape and increasing width and sections 49–61 are in the form of strips of rectangular shape. The cutting sections 43–48 participate in cutting and widening the incision as the blade member B is progressively inserted whereas beyond section 48, the sections 49–61 do not widen the incision but only contribute in increasing the depth of the incision as the blade member B is further inserted. The presence of the cutting edges 42 on sections 49-61 insures substantially effortless insertion of the blade member B. The blade member B can also be used to measure the width of an incision by laying the blade member sideways along the incision. The width of the incision can be determined by the number of strips that the incision spans.

Figure 5A:
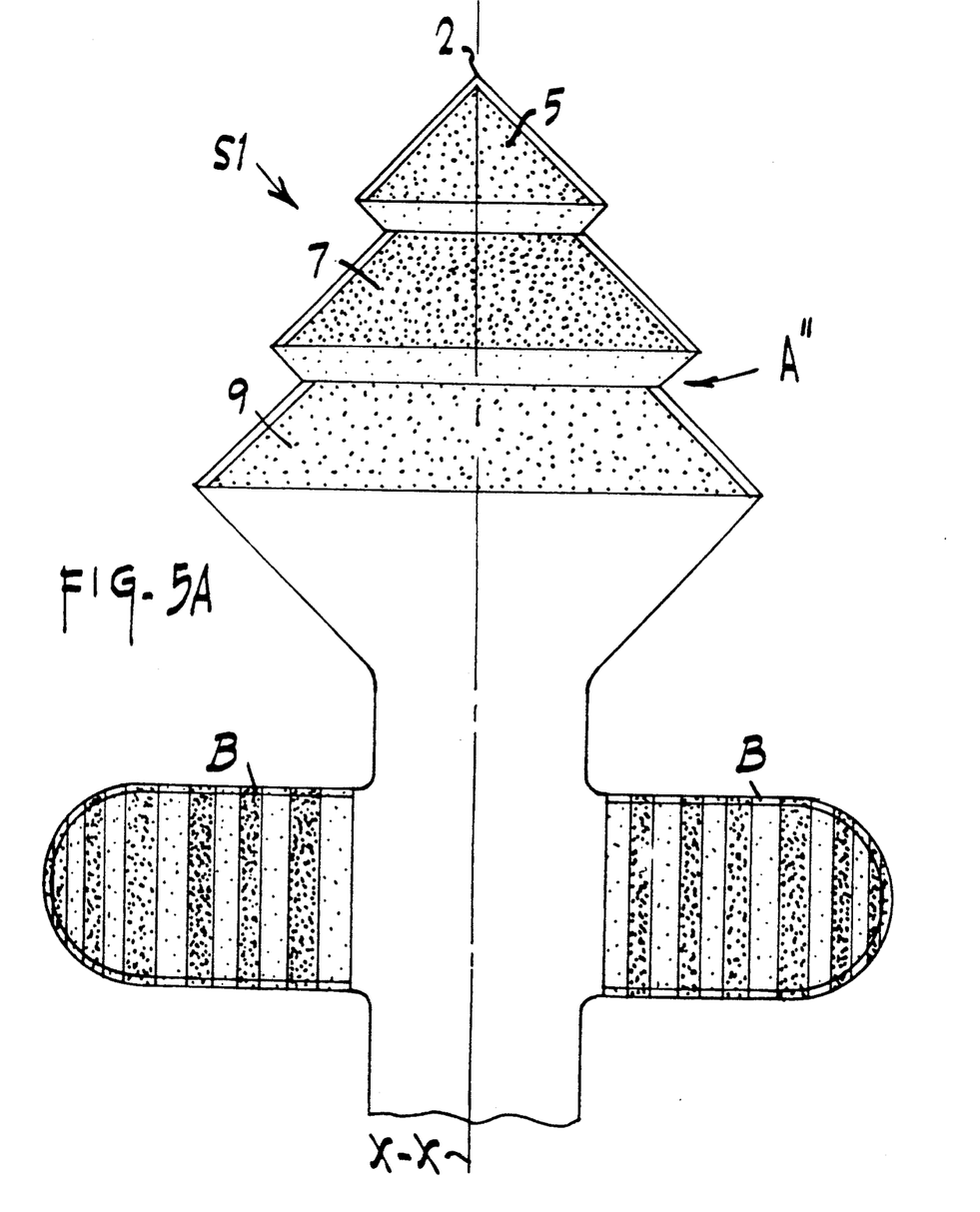
FIG. 5A shows a modification of the scalpel in FIG. 5.

The composite scalpel S of FIG. 5 has blade members A and B thereon which enables selective use of either blade member depending on the particular operation desired. The blade member B extends to the right of the scalpel S and the scalpel is intended for use by right-handed surgeons. If the blade member were to extend to the left of the scalpel, it would be used by left-handed surgeons. In FIG. 5A there is shown a scalpel S1 of universal type in which blade members B extend symmetrically from both sides of the scalpel for use by left and right handed surgeons. In FIG. 5A, the scalpel S1 is illustrated with blade member A" from FIG. 2.

Figure 5B:
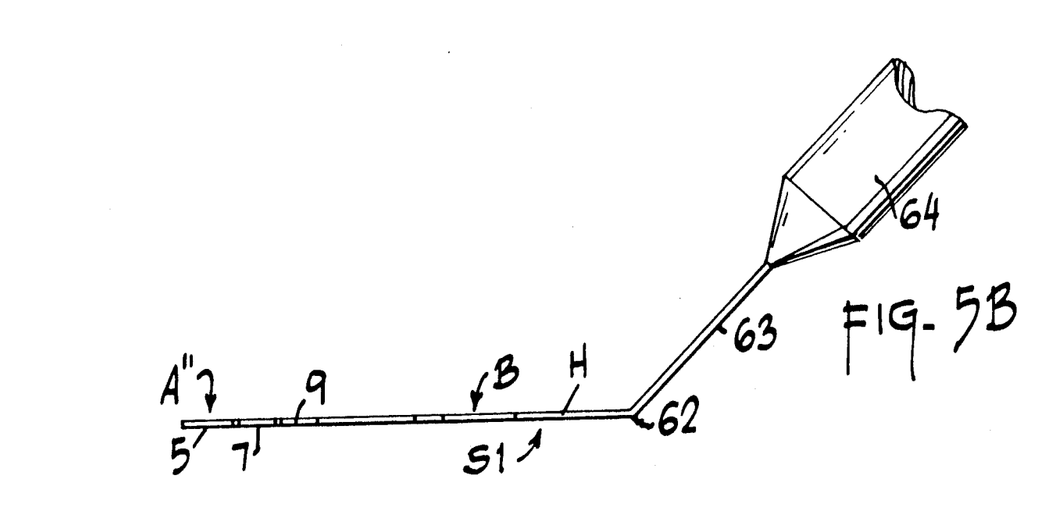
FIG. 5B shows a side elevational view of the scalpel in FIG. 5A.

FIG. 5B shows the scalpel S1 of FIG. 5A in side elevational view. Therein it is seen that the stem H has a 45° bend 62 therein at a position rearwards of the blade members B to form an upwardly extending portion 63. The upwardly extending portion 63 is secured in a handle 64. The attachment of the portion 63 to the handle 64 can be made by a permanent or releasable connection.

Figure 6A:
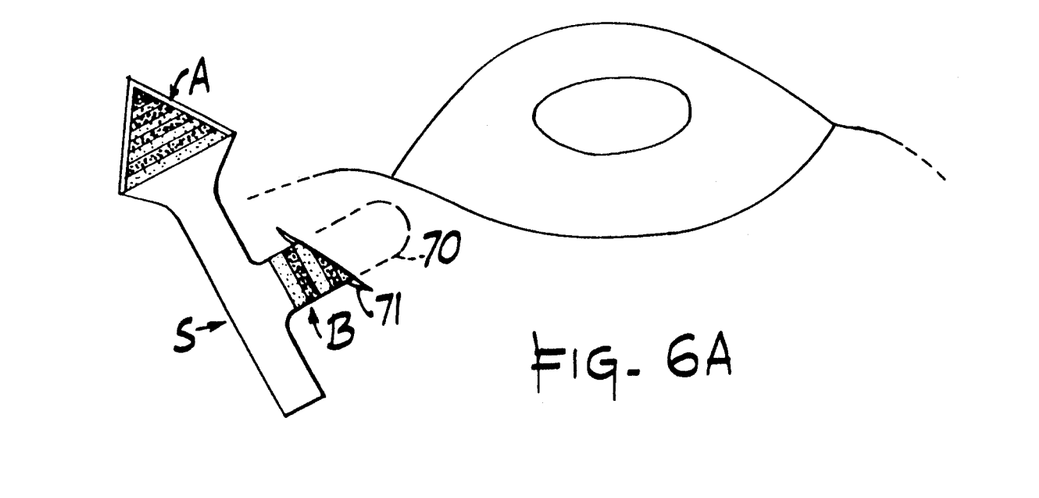
FIGS. 6A-6D are diagrammatic illustrations showing various methods of use of the scalpel.

FIG. 6A shows the blade member B of the scalpel S in FIG. 5 in the formation of a pocket or tunnel 70 in the sclera. After initial formation of a groove in the sclera by the rounded tip of blade member B, the blade member B dissects the scleral tissue to form the pocket 70 by progressive insertion of the blade member B into the scleral tissue.

Figure 6B:
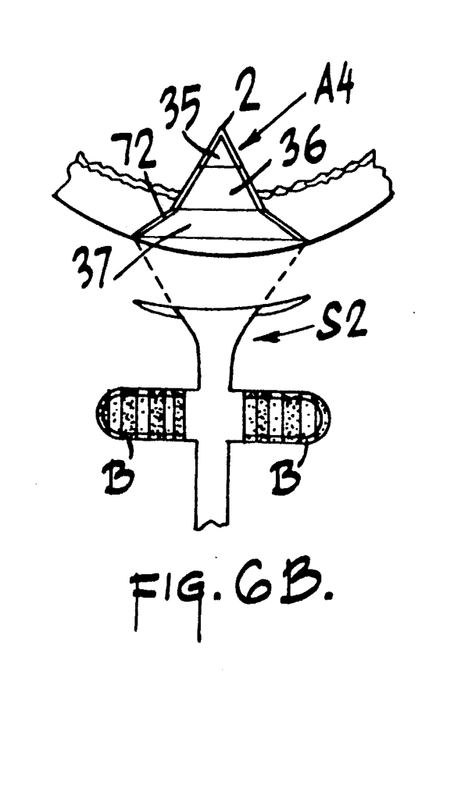

FIG. 6B shows a scalpel S2 having a blade member A4, as shown in FIG. 3A, with left and right scleral dissector blade members B. The blade member A4 is used as a keratome and forms in the sclera an incision 72 approximately 3.0 mm wide (at the base of cutting section 36). Because of the transparency of the cornea, the tip 2 and section 35 of the blade member A4 extending through the sclera is visible internally in the eye.

Figure 6C:
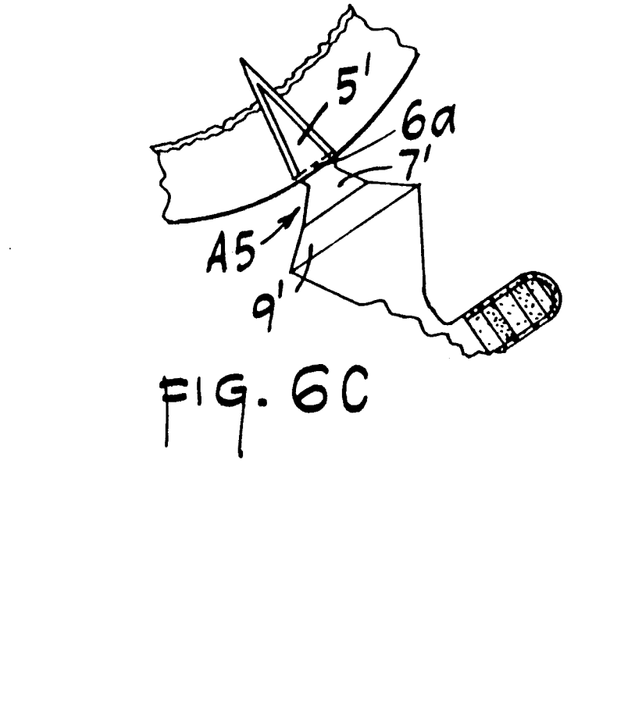

FIG. 6C shows the formation of a small incision or paracentesis in the sclera. The blade member A5 is similar to the blade members in FIGS. 2 and 3A and includes a first cutting section 5' of a length of about 3 mm and a width at its base of 1.5 mm width. When the tip of the cutting section 5' pierces the posterior surface of the sclera, a paracentesis of 1.5 mm width will have been formed in the sclera. Cutting section 5' is joined to juxtaposed cutting section 7' by reverse taper section 6a. The cutting edges of section 7' form a greater taper angle than do the cutting edges of cutting section 5'. Section 7' connects to section 9', the latter having cutting edges of greater taper than the cutting edges of section 7'.

Figure 6D:
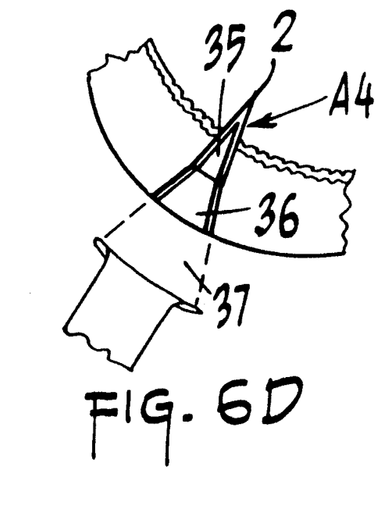

FIG. 6D shows the insertion of blade member A4 of scalpel S2 into the pocket 70 formed by the scleral dissector blade B. The blade member A4 pierces the sclera at the bottom of the pocket and when the tip 2 is visible beneath the cornea, an incision of a width of 3 mm will have been formed in the sclera.

The invention conveniently accomplishes the aforesaid procedures with a multi-function, variable incisional size, color coded, graded blade. The scalpel and blade members described above are not limited to ocular surgery, but are applicable to other modes of surgery requiring dimensional measurements without use of separate instrumentation for carrying out the task of several separate types of surgical scalpels.

The visual distinction of the blade sections can be obtained in a continuous manner with fixed distances represented by individual colors or etched gradations. These are visible when the incisions are made either externally as with the scleral dissector portion of the blade, or internally as with the keratome portions of the blade. The scalpel may include the blade member B serving as a scleral pocket dissector or it may have only the blade member A serving as a keratome portion of varying dimensions and blade configurations.

The use of a color gradient calibration allows direct color verifiable measurements of the instrument both inside and outside the eye. No conventional blades contain this feature.

The blade members A and B can be siliconized or coated with Teflon to minimize tissue drag when dissecting sclera or piercing cornea. Coated surgical blades to minimize tissue drag are not presently in use.

The blade members A and B can have a straight, stepped or curved angulation to allow for differences in preparation of surgical incisions.

The blade members can be shaped for the individual needs of different surgeons, i.e. a single plane vs. a "no stitch" incision.

The invention provides a scalpel having a wide range of unique features with simple component parts of multifunctional use to produce incisions of various sizes. Although the description is addressed to specific embodiments, these should not be construed as limiting the scope of the invention but as merely providing illustrations of some of the presently preferred embodiments of this invention. For example, the blade can be of a larger size for larger skin incisions, or smaller size for use in vascular surgery or in neurosurgery. The shape of the blade need not be of the particular shape as illustrated, but could be ovoid, rectangular, trapezoidal, or square: it can be made of non metallic materials which are able to be sharpened, such as ceramics, glass which is etched or colored, plastics, etc. The blades could be autoclavable if manufactured of a reusable material (i.e. titanium, etc.) but the preferred embodiment is an inexpensive, disposable material.

The scalpel of the invention has a number of features and advantages, namely:

(a) to provide a single blade for cataract surgical procedures rather than requiring several individual blades;

(b) to provide a blade which allows for a convenient and extremely rapid method for measuring an incision's (c) to provide a blade which is both disposable and inexpensive;

(d) to provide a blade which allows for a convenient and extremely rapid method for measuring the width of an incision (i.e. the width of the scleral pocket incision);

(e) to provide a blade whose surface is coated to minimize drag when dissection tissue or piercing the same;

(f) to provide a blade which has multiple purposes in the process of producing incisions of fixed or variable dimensions with visual confirmation of these measurements;

(g) to provide a blade which can be seen inside he eye to determine the width, length, and depth of the incision being produced;

(h) to provide a blade which is color coded for different lengths, widths and depths for the incisions being made;

(i) to provide a blade with markings in color or with etchings or other surface delineations (i.e. patterns, etc.) which provide a measurement of an incision's dimensions;

(j) to provide a blade which can pierce the scleral pocket and produce a specific size internal opening by viewing the blade's color or markings through the cornea to verify the incisional width;

(k) to provide a blade which allows enlargement of an initial incision (scleral pocket or other) to a specific or variable size by viewing the blade's markings or color through the cornea to verify the incisional width;

(l) to provide a scalpel which can make the initial piercing incision, the scleral groove incision, the scleral pocket incision, the scleral pocket entry incision, the phakoemulsifier incision, and the enlarged implant incision; and (m) to provide a blade member which performs the above functions for right and left handed surgeons without having to alter the structure of the blade due to its symmetrical configuration.

What is claimed is:

1. A scalpel for eye surgery comprising a first blade member including a plurality of juxtaposed cutting sections arranged successively along the blade member, said cutting sections having respective cutting edges defining for said cutting sections respective widths and lengths, and means associated with each of said cutting sections for visually delineating said sections from one another such that each cutting section will visually indicate the depth and width of an incision made by inserting said blade member into a body to the depth of the respective said cutting section, a second blade member, and a common support for said first and second blade members, the cutting section of said first blade member at said one end of said first blade member having a pointed tip, said cutting sections increasing in width in the the direction from said one end of the first blade member to the other end of the first blade member, said second blade member being of substantially uniform width and being rounded at one end of said second blade.

2. A scalpel as claimed in claim 1 wherein each section of said first blade member increases in width in the direction of the blade member from one end of the blade member towards the other end of the blade member.

3. A scalpel as claimed in claim 1, said first blade member further comprising an intermediate section between successive cutting sections, said intermediate section having a width which does not exceed the width of the adjacent cutting section closer to said one end of the blade member.

4. A scalpel as claimed in claim 1 wherein said means for visually delineating said cutting sections from one another comprises a different color for each cutting section.

5. A scalpel as claimed in claim 1 wherein said means for visually delineating said sections from one another comprises a distinctive and separate shape for each section.

6. A scalpel as claimed in claim 1 wherein the cutting section at said one end of the first blade member has a pointed tip, the width of said cutting sections progressively increasing from said one end of the first blade member to the other end of the first blade member.

7. A scalpel for eye surgery comprising a blade member having an entry tip and including a plurality of juxtaposed cutting sections arranged successively along the blade member, said cutting sections having respective cutting edges defining for said cutting sections respective widths and lengths, and means associated with each of said cutting sections for visually delineating said sections from one another such that each cutting section will visually indicate the depth and width of an incision made by inserting said blade member into a body to the depth of the respective said cutting section, said blade member having a generally triangular shape and said cutting sections being constituted as successive strips extending parallel to a base of the triangular shaped blade member.

8. A scalpel as claimed in claim 7 wherein each said section includes a perimetral edge region, said cutting edge of each section comprising a portion at said edge region which tapers in thickness.

9. A scalpel as claimed in claim 7, wherein said means for visually delineating said cutting sections from one another comprises surface markings on said cutting sections.

10. A scalpel as claimed in claim 7, wherein selected ones of said strips have different rates of taper at the edges of said cutting sections.

11. A scalpel as claimed in claim 7, wherein said means for visually delineating said cutting sections from one another comprises a different color for each cutting section.

12. A scalpel as claimed in claim 11 wherein said intermediate sections diminish in width in the direction from said one end of the blade member to the other end of the blade member.

13. A scalpel as claimed in claim 11 wherein said intermediate sections have the same width as the adjacent cutting section closer to said one end of the blade.

14. A scalpel as claimed in claim 1, wherein said means for visually delineating said cutting sections from one another comprises surface markings on said cutting sections.

15. A scalpel as claimed in claim 14 wherein each said section includes a perimetral edge region, said cutting edge of each section comprising a portion at said edge region which tapers in thickness.

16. A scalpel as claimed in claim 14 wherein said markings on the exposed surfaces of each section comprise a different coloration on each section on the exposed surface thereof.

17. A scalpel as claimed in claim 14 wherein said blade member has a substantially uniform width and is rounded at said one end for effecting scleral dissection.

18. A scalpel as claimed in claim 17 wherein each said section includes a perimetral edge region, said cutting edge of each section comprising a portion at said edge region which tapers thickness.

19. A scalpel for eye surgery comprising a blade member including a plurality of juxtaposed cutting sections arranged successively along the blade member, said cutting sections having respective cutting edges defining for said cutting sections respective widths and lengths, and means associated with each of said cutting sections for visually delineating said sections from one another such that each cutting section will visually indicate the depth and width of an incision made by inserting said blade member into a body to the depth of the respective said cutting section, each cutting section including a perimetral edge region, said cutting edge of each cutting section comprising a portion at said edge region which tapers in thickness, said cutting sections including widening sections increasing in width in the direction of the blade member from one end towards the other end of the blade member and an intermediate section between successive widening sections, said intermediate section having a width which does not exceed the width of the adjacent widening section closer to said one end of the blade.

20. A scalpel as claimed in claim 19, wherein said means for visually delineating said cutting sections from one another comprises a different color for each cutting section.

21. A scalpel for eye surgery comprising a blade member including a plurality of juxtaposed cutting sections arranged successively along the blade member, said cutting sections having respective cutting edges defining for said cutting sections respective widths and lengths, and means associated with each of said cutting sections for visually delineating said sections from one another such that each cutting section will visually indicate the depth and width of an incision made by inserting said blade member into a body to the depth of the respective said cutting section, said cutting sections extending as lateral strips between said cutting edges and providing respective exposed surfaces, said means for visually delineating said sections from one another comprising markings on said exposed surfaces distinguishing each section from the other, said sections being calibrated as regards width and length so that the visually delineating markings represent the width of the blade member between its cutting edges and the distance from a tip end of the blade to said cutting edges.

22. A scalpel as claimed in claim 21, wherein the cutting section at said one end of the blade member has a pointed tip, the width of the cutting sections progressively increasing from said one end of the blade member to the other end of the blade member.

23. A scalpel as claimed in claim 5 wherein said cutting edges of said cutting sections are disposed at side edges of the blade member, said blade member being flat and said cutting edges being tapered in thickness.

24. A scalpel for eye surgery comprising a blade member having opposed side cutting edges and a plurality of successive juxtaposed bands extending transversely of the blade member between said cutting edges, each band being delineated from adjacent bands by means associated with each band providing a distinctive visual appearance thereof, said bands including widening sections having widths that increase in a direction from a tip end of the blade member to a base of the blade member, an intermediate buffer section between successive widening sections, said intermediate buffer section having a different shape than said widening sections so that said bands are each distinguished by its size and shape.

25. A scalpel as claimed in claim 24 wherein each band has a calibrated width and depth so that the visual appearance of each band is correlated both to the depth of penetration produced by insertion of the blade member into a body and the width of an incision produced by the cutting edges of said band.

26. A scalpel as claimed in claim 24 wherein said means providing the distinctive visual appearance of the bands comprises surface markings on said bands.

27. A scalpel as claimed in claim 26 wherein each band has a calibrated width and depth so that the visual appearance of each band is correlated both to the depth of penetration produced by insertion of the blade member into a body and the width of an incision produced by the cutting edges of said band.

* * * * *